United States Patent [19]
Thomas et al.

[11] Patent Number: 5,705,636
[45] Date of Patent: Jan. 6, 1998

[54] CYCLOHEXENE DERIVATIVES

[75] Inventors: Russell John Thomas; Stefano Biondi; Tino Rossi; Stefania Anna Contini, all of Verona, Italy

[73] Assignee: Glaxo Wellcome S.p.A., Verona, Italy

[21] Appl. No.: 570,820

[22] Filed: Dec. 12, 1995

Related U.S. Application Data

[63] Continuation of Ser. No. 214,847, Mar. 18, 1994, abandoned.

[30] Foreign Application Priority Data

Mar. 20, 1993 [GB] United Kingdom ............. 9305806

[51] Int. Cl.⁶ .................................. C07D 205/08
[52] U.S. Cl. .................... 540/200; 540/302; 540/362
[58] Field of Search ........................ 540/200, 302, 540/362; 548/952, 428

[56] References Cited

U.S. PATENT DOCUMENTS 5,196,528  3/1993  Perboni et al. ................ 540/200

FOREIGN PATENT DOCUMENTS 0 416 953  3/1991  European Pat. Off. .
0 422 596  4/1991  European Pat. Off. .
0161354    9/1984  Japan ................... 548/952
5086062    4/1993  Japan ................... 540/302

OTHER PUBLICATIONS

Reider et al., *Tetrahedron Letters*, 23, 4, 379–382, 1982.

*Primary Examiner*—Jacqueline Haley
*Attorney, Agent, or Firm*—Bacon & Thomas

[57] ABSTRACT

Compounds of the formula

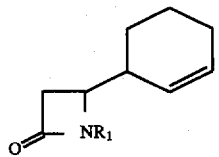
(I)

wherein $R_1$ represents hydrogen or a nitrogen protecting group, useful as intermediates in the preparation of compounds having antibacterial activity.

14 Claims, No Drawings

CYCLOHEXENE DERIVATIVES

This application is a Continuation of application Ser. No. 08/214,847, filed Mar. 18, 1994, now abandoned.

This invention relates to novel cyclohexene derivatives useful in the preparation of compounds having antibacterial activity and to processes for their preparation.

European patent applications EPA Nos. 0416953A and 0422596A2 describe a novel class of tricyclic antibacterial agents and processes for their preparation. The present invention relates to novel intermediates which are particularly useful for preparing compounds within this class of tricyclic antibacterial compounds.

Thus the present invention provides compounds of the general formula (I)

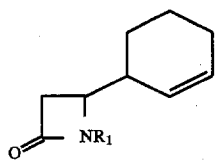

wherein $R_1$ is a hydrogen atom or a nitrogen protecting group.

The compounds of formula (I) contain two centres of asymmetry, one at 4 position of the lactam ring and the other at the 3' position of the cyclohexene ring. For each centre of asymmetry there are two possible configurations which may be designated R and S in the conventional manner according to the rules of Cahn, Ingold and Prelog, Experientia 1956, 12,81. The compound of formula (I) includes both the (4R), (3'S) isomer and the (4S), (3'R) isomer and mixtures thereof, including the racemate thereof.

Examples of suitable nitrogen protecting groups $R_1$ include tri($C_{1-6}$alkyl)silyl e.g. trimethylsilyl and t-butyldimethylsilyl, $C_{1-4}$alkythio e.g. methylthio, $C_{1-6}$alkoxymethyl e.g. methoxymethyl, optionally substituted benzyloxymethyl e.g. benzyloxymethyl or p-methoxybenzyloxymethyl, or $C_{1-6}$alkylsilyloxymethyl e.g. t-butyldimethylsilyloxymethyl.

Conveniently the nitrogen protecting group $R_1$ is tri ($C_{1-6}$alkyl)silyl e.g. trimethylsilyl or more particularly t-butyldimethylsilyl.

Preferred compounds of formula (I) are those which comprise of at least 50% of the (4R) (3'S) isomer (Ia) and more preferably 70–100% e.g. 85–100% of the (4R) (3'S) isomer (Ia).

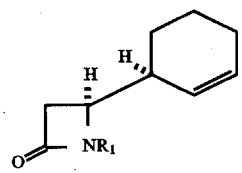

Preferred compounds of formula (Ia) include those wherein $R_1$ is hydrogen or a tri($C_{1-6}$alkyl)silyl group e.g. trimethylsilyl or more particularly t-butyldimethylsilyl.

The compound of formula (I) wherein $R_1$ is hydrogen may be prepared from the reaction of the azetidinone (II)

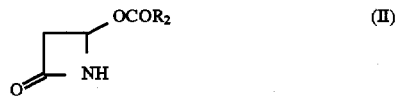

wherein $R_2$ represents $C_{1-4}$alkyl or an optionally substituted phenyl group with the borane derivative (III)

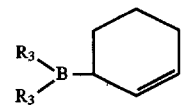

wherein each of $R_3$ represents a $C_{6-10}$cycloalkyl group or the two $R_3$ groups together represent a 1,5-cyclooctadiyl grouping. When $R_3$ represents a $C_{6-10}$cycloalkyl grouping this may be for example monocycloalkyl group e.g. cyclohexyl, or 2-methylcyclohexyl or a bicycloalkyl group e.g. isopinocampheyl.

The reaction is carried out in a solvent such as an ether e.g. tetrahydrofuran or a hydrocarbon e.g. toluene or hexane or mixtures thereof, a halohydrocarbon e.g. dichloromethane or a halobenzene e.g. chlorobenzene or acetonitrile and in the presence of a suitable Lewis acid catalyst such as a titanium tetraisopropoxide, or aluminium triisopropoxide, dialkyl zinc, e.g. diethylzinc, tri-alkyl aluminium e.g. triethylaluminium or alkyl boranes such as triethylborane.

In a preferred embodiment of this process compounds of formula (I) which comprises of at least 70% of the (4R)(3's) isomer of general formula (Ia) may be obtained by the use of a borane derivative (III) wherein $R_3$ is a 2-methyl cyclohexyl or more particularly isopinocampheyl group. In this embodiment particularly useful Lewis acid catalysts include titanium tetraiospropoxide or diethyl zinc.

Compounds of formula (I) wherein $R_1$ represents a nitrogen protecting group may be prepared from the corresponding compound of formula (I) wherein R is hydrogen using conventional means for introducing such nitrogen protecting groups e.g. reaction with the group $R_1X$ wherein X is a leaving group e.g. halogen or methanesulphonate.

Thus for example compounds of formula (I) wherein $R_1$ represents a trialkylsilyl group may be prepared from the corresponding compound of formula (I) wherein $R_1$ is hydrogen by reaction with the appropriate trialkylsilyl halide e.g. chloride in the presence of a suitable base e.g. a tertiary amine such as triethylamine. The reaction is preferably carried out in a polar aprotic solvent such as N,N-dimethylformamide.

Compounds of formula (I) wherein $R_1$ represents an alkylthio group may be prepared by reaction of the corresponding compound of formula (I) wherein $R_1$ represents hydrogen by reaction with the appropriate alkylthiomethanesulphonate, preferably in the presence of a base such as lithium bis(trimethylsilyl)amide.

The azetidinones (II) are either known compounds or may be prepared by analogous methods to that described for the known compounds.

Preferred azetidinones for use in the reaction include compounds of formula (II) wherein $R_2$ is methyl or more particularly phenyl.

The borane derivatives (III) may be prepared by reaction of the borane $(R_3)_2BH$ (IV) with cyclohexadiene in a solvent such as a hydrocarbon e.g. hexane or an ether e.g. tetrahydrofuran at a temperature within the range −78° to +30°.

The borane compounds (IV) are either known compounds or may be prepared by analogous methods to that described. Thus boranes (IV) in which $R_3$ is a cycloalkyl group may be prepared from the reaction borane dimethylsulphide complex with the appropriate cycloalkene corresponding to $R_3$. This reaction is preferably carried out in a solvent such as an ether e.g. tetrahydrofuran or diethyl ether.

A preferred borane derivative (III) for use in the reaction is that prepared from the cycloalkene 1S-(−)-alpha-pinene. A further preferred borane derivative (III) for use in the reaction is that prepared from 2-methylcyclohexene.

The compounds of formula (Ia) wherein $R_1$ is a nitrogen protecting group may be converted into compounds of formula (V)

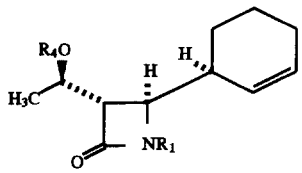
(V)

wherein $R_4$ is tri $(C_{1-4}$alkyl)silyl and $R_1$ is a nitrogen protecting group, by reaction with the ketone $R_4COCH_3$ wherein $R_4$ is tri($C_{1-4}$alkyl)silyl. The reaction may be carried out by treating a compound of formula (I) with a suitable base such as lithium diisopropylamide in a solvent such as tetrahydrofuran followed by addition of the ketone $R_4COCH_3$ followed by potassium t-butoxide.

Compounds of formula (V) in which $R_1$ is a hydrogen atom may be prepared from the corresponding compound of formula (V) wherein $R_1$ is a nitrogen protecting group by conventional known means for the removal of such nitrogen protecting groups. Thus for example when $R_1$ is a t-butyldimethylsilyl group this may be selectively removed by reaction with tetrabutylammonium fluoride and glacial acetic acid in a solvent such as tetrahydrofuran.

The compounds of formula (V) in which $R_1$ is hydrogen may be converted into known antibacterial agents using the procedures described in EPA 0416953A2.

The process described above for preparing the compounds of formula (V) from the azetidinone (II) via the novel compounds of formula (I) and more particularly the (4R) (3'S) enantiomer thereof (Ia), has the advantage over known processes in that it gives the a good yield of the required isomer from readily available starting materials and represents a further aspect of the invention.

In order that the invention may be more fully understood the following examples are given by way of illustration only.

Infra-red spectra were measured in chloroform-disolution on an FT-IR instrument. Proton Magnetic Resonance ($^1$H-NMR) were recorded at 400 MHz. Chemical shifts are reported in ppm downfiled (d) from $Me_4Si$, used as an internal standard. All temperatures are in °C. Tlc refers to thin layer chromatrograph on silica plates. Dried refers to solutions dried over anhydrous sodium sulphate. e.e refers to enantiomeric excess.

EXAMPLE 1

(−)-Erythro-(4R)-4-[(3'S)-Cyclohexen-3-yl]-azetidin-2-one

Method A (1S)-(−)-alpha-pinene (12 ml of 82% e.e.) was added over 15 min to a stirred solution of borane dimethylsulphide complex (3 ml of a 2M solution in tetrahydrofuran) at 0° under a nitrogen atmosphere. The mixture was stirred for 3 hours then (1S)-(−)-alpha-pinene (10 ml of 82% e.e.) was added in 15 min and the stirring immediately stopped. The reaction was allowed to stand at 0° for 16 hours. The supernatant liquor was removed and the precipitate was washed twice with anhydrous tetrahydrofuran (20 ml) at −10°, then dried under reduced pressure. The solid was suspended in anhydrous tetrahydrofuran (30 ml) at −25° under a nitrogen atmosphere, 1,3-cyclohexadiene (7.5 ml) was added and the resulting mixture was stirred for 40 hours. 4- Benzoyloxyazetidin-2-one (1.91 g) was added to the solution at −25° and to this mixture was added titanium tetraisopropoxide (4.5 ml). After 6 hours titanium tetraisopropoxide (1.5 ml) was added and the reaction was stirred for 16 hours. The mixture was treated with a pH=3 buffered solution of sodium citrate/citric acid (40 ml) (10% w/w) and extracted twice with ethyl acetate (200 ml). The organic phase was washed with brine (2×100 ml), dried, concentrated. The crude material was redissolved in n-hexane (100 ml) and extracted with acetonitrile (200 ml). The acetonitrile solution was extracted with n-hexane (3×50 ml) and then, concentrated to give a yellowish solid. This was purified by flash chromatography on silica gel eluting with a mixture 70% cyclohexane: 30% ethyl acetate to give the title compound as a colourless solid (950 mg).

HPLC:
column: Chiralpak AS 25×0.46 cm; temperature 23°; wavelength: 220 mn; mobile phase: 70% ethanol/30% n-hexane; flow rate: 0.8 ml/.min; retention time 9.9 min (area %=84.9 title compound), 22.4 (area % 15.1 (+)-enantiomer); enantiomeric excess: 69.7%

Method B (−)-Erythro-(4R)-4-[(3'S)-Cyclohexen-3-yl]-azetidin-2-one (1S)-(−)-alpha-pinene (9.7 ml of 98% ee) was added over 15 min to a stirred solution of borane dimethylsulphide complex (30 ml of a 2M solution in tetrahydrofuran) at 0° under a nitrogen atmosphere. The mixture was stirred for 3 hours then (1S)-(−)-alpha-pinene (10 ml of 98% ee) was added over 15 min and the stirring immediately stopped. The reaction was allowed to stand at 0° for 16 hours. The supernatant liquor was removed and the precipitate washed twice with anhydrous tetrahydrofuran (20 ml) and cooled to −10°, then dried under reduced pressure. The solid was suspended in anhydrous tetrahydrofuran (30 ml) at 25° under a nitrogen atmosphere, and (1S)-(−)alpha-pinene (3 ml of 98% e.e.) added. 1,3-cyclohexadiene (9.3 ml) was added and the resulting mixture was stirred for 20 hours. A solution of 4- Benzyloxyazetidin-2-one (2.0 g) in anhydrous tetrahydrofuran (10 ml) was added to the reaction at −25° followed by diethylzinc (49.1 ml of a 1.1M solution in toluene). The reaction was then stirred at −25° C. for 5 hours. The mixture was treated with a pH=3 buffered solution of sodium citrate/citric acid (40 ml) (10% w/w) and extracted twice with ethyl acetate (200 ml). The organic phase was washed with brine (2×100 ml), dried, concentrated. The crude material was redissolved in n-hexane (100 ml) and extracted with acetonitrile (200 ml). The acetonitrile solution was extracted with n-hexane (3×50 ml), concentracted to give a yellowish solid containing the title compound. Purification by flash chromatography on silica gel eluting with a mixture 70% cyclohexane: 30% ethyl acetate gave the title compound as a colourless solid (940 mg). $[\alpha]D=−103.6(CHCl_3, c=1.065)$ HPLC:
column: Chiralpak AS 25×0.46 cm; temperature 23°; wavelength: 220 mn; mobile phase: 70% ethanol/30% n-hexane; flow rate: 0.8 ml/.min; retention time 9.9 min (area %=93.9 title compound), 22.4 (area % 6.1 (+)-enantiomer); enantiomeric excess: 87.8%

EXAMPLE 2

(±)-Erythro-(4R S)-4-[(3'RS)-Cyclohexen-3-yl]-azetidin-2-one 1,3 cyclohexadiene (1.05 ml) was added to a solution of borabicyclononane (20 ml of a 0.5M solution in hexanes) at room temperature under a nitrogen atmosphere and the mixture was stirred for 24 hours. Dry tetrahydrofuran (80 ml), was added followed by a solution of 4-benzyoloxyazetidin-2-one (1.53 g) in dry tetrahydrofuran (10 ml). Diethylzinc (8 ml of a 1M solution in hexanes) was then added and the reaction stirred for 3 hours. A sodium citrate/citric acid pH 3 buffer solution (100 ml) was added to the reaction mixture which was then stirred for 2 hours. The aqueous layer was extracted with ethyl acetate (200 ml) and the combined organic phases washed with saturated sodium bicarbonate (100 ml) brine (2×50 ml) and dried. The solvent was removed under reduced pressure and the title compound was isolated, by flash chromatography on silica gel eluting with mixtures of ethyl acetate in cyclohexane increasing from 10% to, 40% with respect to ethyl acetate, as a colourless oil (485 mg).

IR V max (cm-1): 3254(NH), 1755(C=O-lactam). $^1$H-NMR ($\delta$, ppm, CDCl$_3$): 5.99 (s broad, 1H), 5.85 (m, 1H), 5.52 (m,1H), 3.47 (m, 1H), 2.97 (ddd, 1H), 2.70 (ddd, 1H), 2.32-2.22 (m, 1H), 2.10-1.94 (m, 2H), 1.90-1.70 (m, 2H), 1.62-1.48 (m, 1H), 1.30-1.20 (m, 1H).

EXAMPLE 3

(±)-erythro-(4RS)-4-[(3'RS)-Cyclohexen-3-yl]-azetidin-2-one

Into a 500 ml 3-necked flask fitted with a thermometer and septa was introduced cyclohexene (21 ml) and dry diethyl ether (50 ml). The solution was cooled to −5° with stirring, and borane dimethylsulphide complex (50 ml of a 2M solution in tetrahydrofuran) was slowly added. The reaction mixture was stirred for 4 hours then allowed to stand for a further 2 hours. The resulting mixture was concentrated under reduced pressure. The white solid was suspended in dry tetrahydrofuran (80 ml) at room temperature under an atmosphere of nitrogen, 1,3-cyclohexadiene (10 ml) was added and the resulting mixture was stirred for 18 hours. 4-benzyoloxyazetidin-2- one (5.74 g) was added to the solution and the resulting mixture cooled to −50°. Diethylzinc (30 ml of a 1.1M solution in toluene) was added and the reaction stirred for 4 hours before allowing the reaction to warm to room temperature. After a further 1 hour, the reaction was cooled to −70° and glacial acetic acid (10 ml) added. The reaction mixture was allowed to reach room temperature and then stirred overnight. Ethyl acetate (300 ml) was added, the organic phase neutralised by washing with saturated aqueous sodium carbonate, dried with brine and anhydrous sodium sulphate prior to being filtered and the solvents removed under reduced pressure. The title compound was isolated from the residue by flash chromatography on silica gel, eluting with 30% ethyl acetate 70% cyclohexane, as a colourless oil (4.53 g).

EXAMPLE 4

(4R)-1-t-Butyldimethylsilyl-4-[(3'S)-cyclohexen-3-yl]-azetidin-2-one

The compound of Example 1 (3.3 g) was dissolved in dry dimethylformamide (50 ml) and to it added t-butyldimethylsilyl chloride (3.8 g) and triethylamine (4 ml) at room temperature under a nitrogen atmosphere. The reaction was then stirred for 2 hours prior to the addition of diethyl ether (300 ml) and the solution washed with citric acid/sodium citrate pH 3 buffer (2×200 ml), monopotassium phosphate/dipotassium phosphate pH 7 buffer (100 ml), and brine (50 ml) prior to being dried, filtrered and the solvent removed under reduced pressure. The title compound was isolated from the crude residue by flash chromatography on silica gel, eluting with 10% ethyl acetate 90% cyclohexane, as a colourless oil (5.0 g).

IR V max (cm-1): 1724 (C=O-lactam) $^1$ H-NMR ($\delta$, ppm, CDCl$_3$): 5.94-5.87 (m, 1 H), 5.74-5.67 (m, 1H), 3.58 (m, 1H), 2.87 (dd, 1H), 2.68 (dd, 1H), 255 (m, 1h), 2.10-1.92 (m, 2H), 1.82-1.74 (m,), 1.62-1.48 (m), 1.14-0.98 (m, 1H), 0.96 (s, 9H), 0.28 (s, 3H), 0.20 (s, 1H).

EXAMPLE 5

(3S, 4R)-1-t-Butyldimethylsilyl-4-[(3'S)-cyclohexen-3-yl]-3-[(1R)-1-t-butyldimethylsilyloxyethyl]-azetidin-2-one A solution of lithium diisopropylamide was prepared by the dropwise addition of n-butyllithium (1.38 ml of a 2M solution in hexanes) to a cooled (−78°) solution of diisopropylamine (0.38 ml) in dry tetrahydrofuran (10 ml) under a nitrogen atmosphere. The resulting solution was stirred for 30 min at −78°. A solution of the compound of Example 4 (660 mg) in dry tetrahydrofuran (15 ml) was added over 10 min. The resulting solution was stirred for a further 5 min and then a solution of methyl t-butyldimethylsilylketone (0.44 g) in of dry tetrahydrofuran (5 ml) was added. The reaction was stirred for 10 min at −78° before the addition of a solution of potassium t-butoxide (0.31 g) in t- butanol (1.8 ml) over 10 min. The reaction was allowed to warm to 0° over 10 min., quenched by the addition of saturated aqueous ammonium chloride (4 ml), and then diluted with ethyl acetate (15 ml). The organic phase washed with water (5 ml) and brine (5 ml) prior to being dried. After filtration, the solvents were removed under reduced pressure, xylene (20 ml) added and the solvent removed under reduced pressure. The title compound was isolated from the residue by silica gel chromatography eluting with a mixture of 5% ethyl acetate in cyclohexane (Rf=0.27), as a colourless solid (867 mg), mp 62.5°–63.5°

IR V max (cm-1): 1732 (C=O) $^1$H-NMR ($\delta$, ppm, CDCl$_3$): 5.8 (m), 5.7 (m), 4.02 (m), 3.51 (t), 2.79 (dd), 2.5 (m), 2.00 (m), 1.8 (m), 1.2 (m), 1.22 (d), 0.96 (s), 0.88 (s), 0.26 (s), 0.20 (s), 0.07 (s), 0.06 (s).

EXAMPLE 6

(3S,4R)-4-[(3'S)-Cyclohexen-3-yl]-3-[(1R)-1-t-butyldimethylsiloxy ethyl]-azetidin-2-one To a stirred solution of the product of Example 5 (342 mg) in dry tetrahydrofuran (15 ml) was added a solution of tetrabutylammonium fluoride (0.92 ml of a 1.1M solution in tetrahydrofuran containing glacial acetic acid (62 ul)). After 10 min the solution was diluted with ethyl acetate (20 ml) and saturated aqueous sodium bicarbonate (5 ml) added. Following separation of the phases, the organic layer was washed with water (5 ml) and brine (5 ml) prior to being dried, filtrered and the solvents removed under reduced pressure. The title compound was isolated from the resultant residue by silica gel chromatography eluting with 20% ethyl acetate in cyclohexane (Rf=0.24) as a colourless solid (194 mg)

IR V max (cm-1): 3416 (N—H), 1753 (C=O), 1603 (C=C) $^1$H NMR (δ, ppm, CDCl$_3$): 5.82 (m), 5.81 (m), 5.60 (dd), 4.14 (m), 3.46 (dd), 2.85 (m), 2.24 (m), 2.00 (m), 1.85-1.70 (m), 1.54 (m), 1.27 (m), $a_D$=-42.4 (c=1.14 in CHCl$_3$).

We claim:

1. Compounds of the general formula (I)

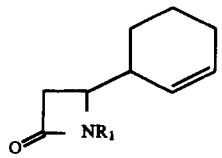
(I)

wherein R$_1$ represents hydrogen or a nitrogen protecting group.

2. A compound of the general formula (Ia)

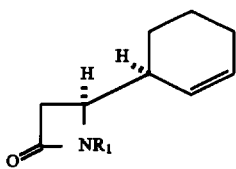
(Ia)

wherein R$_1$ has the meanings defined in claim 1.

3. A compound as claimed in claim 1 wherein R$_1$ is hydrogen or a nitrogen protecting group selected from tri(C$_{1-6}$alkyl)silyl, C$_{1-4}$alkylthio, C$_{1-6}$alkoxymethyl, benzyloxymethyl, p-methoxybenzloxymethyl or C$_{1-6}$alkylsilyloxymethyl.

4. A compound as claimed claim 1 wherein the nitrogen protecting group R$_1$ is tri(C$_{1-6}$alkyl)silyl.

5. (−) Erythro-(4R)-4-[(3'S)-cyclohexen-3-yl]-azetidin-2-one.

6. (4R)-1-t-Butyldimethylsilyl-4-[(3'S)-cyclohexen-3-yl]-azetidin-2-one.

7. A compound as claimed in claim 2 wherein R$_1$ is hydrogen or a nitrogen protecting group selected from tri(C$_{1-6}$alkyl)silyl, C$_{1-4}$alkythio, C$_{1-6}$alkoxymethyl, benzyloxmethyl, p-methoxybenzyloxymethyl or C$_{1-6}$alkylsilyloxymethyl.

8. A compound as claimed in claim 2 wherein the nitrogen protecting group R$_1$ is tri(C$_{1-6}$alkyl)silyl.

9. A compound as claimed in claim 3 wherein the nitrogen protecting group R$_1$ is tri(C$_{1-6}$alkyl)silyl.

10. Compounds of claim 1 which comprise at least 50% of the (4R)(3'S) isomer (1a)

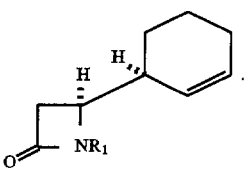
(Ia)

11. Compounds of claim 1 which comprise at least 70% of the (4R)(3'S) isomer (1a)

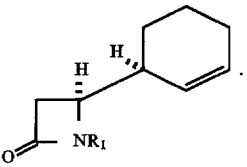
(Ia)

12. Compounds of claim 1 which comprise at least 85% of the (4R)(3'S) isomer (1a)

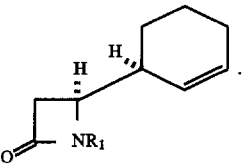
(Ia)

13. Compounds of claim 1 which comprise at least 69% of the (4R)(3'S) isomer (1a)

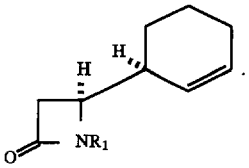
(Ia)

14. Compounds of claim 1 which comprise at least 87% of the (4R)(3'S) isomer (1a)

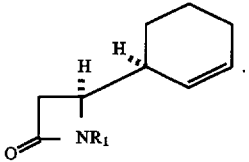
(Ia)

* * * * *